(12) United States Patent
Ortiz et al.

(10) Patent No.: US 6,767,534 B1
(45) Date of Patent: Jul. 27, 2004

(54) POST HAIR REMOVAL SKIN CARE LOTION

(76) Inventors: Robert Ortiz, 83-10 35th Ave. #1V, Jackson Heights, NY (US) 11372; Veronica Fernandez, 83-10 35th Ave. #1V, Jackson Heights, NY (US) 11372

( * ) Notice: Subject to any disclaimer, the term of this patent is extended or adjusted under 35 U.S.C. 154(b) by 124 days.

(21) Appl. No.: 10/251,076

(22) Filed: Sep. 20, 2002

(51) Int. Cl.⁷ .............................. A61K 7/00; A61K 7/15
(52) U.S. Cl. .......................................... 424/73; 424/401
(58) Field of Search ..................................... 424/73, 401

(56) References Cited

U.S. PATENT DOCUMENTS 6,352,691 B1 * 3/2002 Ortiz et al. .................... 424/73

* cited by examiner

*Primary Examiner*—James M. Spear
(74) *Attorney, Agent, or Firm*—Goldstein Law Offices, P.C.

(57) ABSTRACT

A post hair removal skin lotion composition for use in reducing inflammation and irritation of skin immediately following hair removal by shaving, waxing, tweezing, electrolysis, or use of depilatory products, and for repairing skin damage resulting from these methods. The composition comprises deionized water, aloe vera gel, soybean oil, alpha lipoic acid, stearic acid, glyceryl monostearate, propylene glycol, lauramide DEA, vitamin E (tocopherol), hydrocortisone acetate, vitamin C (ascorbic acid), carbomer, hydroxymethylcellulose, methylparaben, propylparaben, and polyquaternium-15.

16 Claims, No Drawings

POST HAIR REMOVAL SKIN CARE LOTION

BACKGROUND OF THE INVENTION

1. Field of the Invention

The invention relates to a post hair removal skin care lotion which is effective in the prevention and treatment of the damage to the skin which is often a by-product of hair removal. The invention also relates to a skin care lotion which will alleviate the accompanying discomfort which is associated with the skin damage caused by hair removal.

The vast majority of adult individuals in our society frequently engage in the process of shaving in order to effect the removal of unwanted hair. In particular, men will often shave daily in order to prevent the growth of unwanted facial hair. Woman will also often employ shaving techniques for the purpose of removing unwanted hair on portions of the body. Although there are some alternatives for removal of unwanted hair, such as electrolysis, waxing, tweezing, or depilatory creams, shaving remains the most common method for the removal of unwanted hair.

During the process of shaving, a sharp blade is scraped against the skin. In order to obtain a "clean-shaven look", unwanted hairs must be cut as closely to the skin as possible. As a result of this, the process is necessarily accompanied by damage to the epidermis of the skin, and may, during accidental cuts to the skin, involve layers of skin below the epidermis. Although various improvements in the shape and configuration of razors have been made, no shaving technique yet exists which does not damage and abrade the skin.

When the skin surface has been broken during shaving, the skin becomes irritated and often inflamed. This is the body's response to skin damage, and it helps to prevent the occurrence of infections, which are caused by entry of bacteria into the body through the damaged skin surface. Symptoms of this inflammatory process may include pain, redness, burning, itching, and dryness. These symptoms may be exacerbated in individuals with sensitive skin. Symptoms may also be more pronounced in individuals who shave on a daily basis, because frequent shaving will not allow the body's natural healing processes to be complete.

Pseudofolliculitis is the medical term which describes an irritated condition of the skin. In men, pseudofolliculitis commonly follows shaving. In women, however, this condition can occur after shaving, waxing, tweezing, electrolysis, or when utilizing depilatory products on the legs, bikini lines, and underarm areas. Often, after shaving, hairs will reemerge from the skin surface only to curl back towards and reenter the skin surface. This process, which leads to "ingrown hairs", is another cause of pseudofolliculitis. Additionally, skin damage may be caused by other hair removal procedures, including waxing or the use of depilatory creams. Regardless of how it is caused, pseudofolliculitis can result in permanent unwanted dark areas on the skin and may detract from the appearance of a clear and healthy complexion.

Few effective treatments for pseudofolliculitis are currently available. Most affected individuals do not have the luxury of avoiding shaving for a prolonged period of time, which is the most effective treatment for this condition. Pseudofolliculitis remains a major challenge among dermatologists and other skin care professionals.

2. Description of the Related Art

My prior U.S. Pat. No. 6,352,691 describes an after-shave skin care lotion which provides immediate and effective relief from symptoms associated with shaving. The prior product provides a composition which is effective in the prevention and treatment of pseudofolliculitis. The prior product contains the naturally occurring antioxidants, tocopherol acetate (vitamin E) and rosehip oil (vitamin C), as well as the anti-inflammatory agent, hydrocortisone acetate, dissolved in a base of aloe vera gel.

Although my prior patent provides an excellent product and is effective in preventing and treating pseudofolliculitis and other skin irritation which is associated with shaving, the present description provides an improved composition which provides additional benefits to the user. These improvements make the current composition even more suitable for the prevention and treatment of skin damage caused by shaving and other processes used for hair removal.

SUMMARY OF THE INVENTION

It is an object of the invention to provide a product that relieves the skin irritation which is caused by the removal of unwanted hair, and which augments the body's physiological repair of damaged skin. Accordingly, this skin care lotion contains hydrocortisone acetate, a safe and powerful anti-inflammatory agent. Topical application of hydrocortisone acetate to the skin provides almost instantaneous relief of irritated skin.

It is another object of the invention to provide an effective treatment for pseudofolliculitis and to prevent long-term damage to the skin. Accordingly, this mixture prevents pseudofolliculitis from developing from the repeated injuries to the skin that are caused by any process of hair removal.

It is yet another object of the invention to provide an effective treatment for pseudofolliculitis which is available without a prescription. Accordingly, this product contains hydrocortisone acetate at a low concentration, and it therefore may be sold without a prescription.

It is a further object of the invention that the skin care lotion may be tolerated by virtually anyone and may be used on any part of the body affected as a result of the removal of unwanted hair. Accordingly, the ingredients in this formulation include nutrients, substances which are beneficial for the skin's surface, and substances which are produced by the body itself, such as hydrocortisone.

It is a still further object of the invention to provide a product which is not difficult to apply and does not unduly lengthen the time required to complete the hair removal process. Accordingly, this product may be easily and conveniently applied within a matter of seconds.

It is another object of this invention to provide a product which contains several antioxidants, to even more greatly prevent the occurrence of free radicals and their associated damage to cell membranes. Accordingly, this product includes vitamin E, vitamin C, soybean oil, and alpha lipoic acid, which have known powerful antioxidant properties, and prevent free radical-induced damage to the skin. These compounds also contain well documented anti-inflammatory properties.

It is yet another object of this invention to provide a cream which is easy to apply and which is smooth and velvety to the touch. Accordingly, this product is fortified with emulsifying agents which facilitate mixing of the oil and water phases and give the product an even creamier consistency.

It is still yet another object of this invention to provide a product which is stable and has a long shelf-life.

Accordingly, this formulation includes up to three different preservatives, each of which contributes to enhanced product stability.

It is a further object of this invention that this product is a thick cream which may be easily handled and applied by the user. Accordingly, this product includes two thickening agents, each of which confers enhanced gel-like properties to the resultant mixture.

It is yet a further object of this invention to provide a mixture which facilitates the uptake of hydrocortisone acetate by the skin. Accordingly, this product contains aloe vera gel, which enhances the absorption of hydrocortisone acetate by the skin.

It is a still further object of this invention to help moisturize the skin, which tends to dry out after the hair removal process. Accordingly, this product contains propylene glycol which helps the skin attract and retain moisture.

The invention is an improved post hair removal skin care lotion which is useful in reducing inflammation and irritation of the skin which follows hair removal by any process, and for repairing the accompanying skin damage. The composition contains aloe vera gel, vitamin C (ascorbic acid), vitamin E (tocopherol), and hydrocortisone acetate, each of which are present in my prior patent. Additionally, the composition contains two emulsifying agents, namely stearic acid and glyceryl monostearate, which both facilitate the mixing of the oil and water interphase which results from mixing hydrophobic and hydrophilic substances in a single product. Moreover, this product includes three preservatives, namely methylparaben, propylparaben, and polyquaternium-15, which contribute to the stability of the product and increase its shelf-life. Also included are two thickening agents, namely carbomer and hydroxypropyl methylcellulose, which make the resulting cream thicker and more easily applied.

To the accomplishment of the above and related objects the invention may be embodied in the form described in the following description. Attention is called to the fact, however, that the examples given are illustrative only. Variations are contemplated as being part of the invention, limited only by the scope of the claims.

DETAILED DESCRIPTION OF THE PREFERRED EMBODIMENTS

The present invention is a composition of matter which provides relief of symptoms and discomforts associated with hair removal and will be referred to as a post hair removal skin care lotion. The preferred composition comprises up to sixteen ingredients, each of which functions to confer one or more than one beneficial property to the combination of substances.

The first four ingredients described are present in applicant's prior U.S. Pat. No. 6,352,691, which applicant hereby incorporates by reference. These four ingredients are aloe vera extract, vitamin C, vitamin E, and hydrocortisone acetate.

Aloe vera has well documented moisturizing and moisture balancing properties. Aloe vera also has bactericidal properties and kills bacteria before they can enter the damaged skin.

Vitamin C, chemically known as ascorbic acid, is important in the synthesis of collagen, an important structural component of skin. Consequently, vitamin C is vital for skin regeneration. Vitamin C is also a powerful antioxidant.

Vitamin E, chemically known as tocopherol acetate, is also a powerful biological antioxidant. It prevents destruction of cell membranes from oxidative destruction by reducing the occurrence of free radicals. Vitamin E is also implicated in cell division, and therefore greatly assists the regenerative process.

Hydrocortisone acetate is the primary anti-inflammatory agent in the composition and is useful in reducing the effects of pseudofolliculitis. Hydrocortisone acetate is a corticosteroid which provides temporary relief from itching, minor irritations, and rashes when applied topically to the skin. Topical application of hydrocortisone acetate may cause systemic absorption, which may lead to a decrease in the production of steroid hormones by the body. However, low doses of topically applied hydrocortisone acetate will not cause this problem.

In addition to these four ingredients, the present formulation includes up to twelve other pure substances or mixtures of substances. Of these twelve additional ingredients, two are antioxidants, two are emulsifying agents, three are preservatives, and two are thickeners. The remaining three ingredients are propylene glycol, lauramide DEA, and deionized water. The benefits of each of these additional ingredients over my prior patent will be discussed in turn.

The additional antioxidizing agents contained in this improved formulation are soybean oil and alpha lipoic acid. Soybean oil is actually a mixture of substances, and it acts as an antioxidant by preventing free radicals from forming and damaging cells and tissues. It helps with cell membrane formation and accelerates the regeneration and stabilization of membranes. Alpha lipoic acid is a natural molecule found in every living cell of the human body. It is a powerful antioxidant and anti-inflammatory compound. Further, the alpha lipoic acid serves to greatly enhance the functions and effects of the vitamins C and E.

The emulsifying agents are stearic acid and glyceryl monostearate. These agents facilitate the mixing of the oil and water phases of this product and thereby provide a homogenous, single phase product.

The three preservatives are methylparaben, propylparaben, and polyquaternium-15. These compounds function to inhibit the growth of bacteria and to prevent the degradation of the product that would occur in their absence.

The two thickeners are carbomer and hydroxypropyl methylcellulose. These compounds give the product a thicker consistency, and provide for easier application onto the skin surface by the user.

The remaining three ingredients are propylene glycol, lauramide DEA, and deionized water. Propylene glycol has several functions. It acts as a solvent to help dissolve the hydrocortisone into solution. Additionally, it acts as a preservative and a moisturizing agent.

Lauramide DEA acts as a surfactant by decreasing surface tension and allows for smoother skin application and absorption. It also functions to help maintain the cream at a normal pH.

The final ingredient of the skin care lotion is the deionized water, which acts as a vehicle/solvent for the other ingredients. The deionized water is present in the amount which maximizes ease of application of the product, by giving it a consistency that allows the cream to be easily spread onto the skin. Further, the deionized water serves to maintain the proper hydration to the skin.

Now that the major components of the composition have been outlined, the preferred proportions are as follows:

aloe vera gel at a weight percent of 6.021–7.359%;
soybean oil at a weight percent of 6.021–7.359%;

stearic acid at a weight percent of 3.51–4.29%;

glyceryl monostearate at a weight percent of 3.006–3.674%;

propylene glycol at a weight percent of 2.511–3.069%;

lauramide DEA at a weight percent of 1.35–1.55%;

tocopherol at a weight percent of 0.405–0.495%;

hydrocortisone acetate at a weight percent of 0.180 0.500%;

alpha lipoic acid at a weight percent of 0.180–1.25%;

ascorbic acid at a weight percent of 0.198–0.242%;

carbomer at a weight percent of 0.198–0.242%;

hydroxypropyl methylcellulose at a weight percent of 0.198–0.242%;

methylparaben at a weight-percent of 0.198–0.242%;

propylparaben at a weight percent of 0.099–0.121%; and polyquaternium-15 at a weight percent of 0.09–0.11%.

Deionized water makes up the balance of the product according to the proportions of the other ingredients.

The post hair removal skin care lotion composition as previously described, can be applied once, immediately following hair removal by shaving, waxing, tweezing, electrolysis, or use of depilatory products. Multiple applications (i.e. more than three per day) within a single day are not recommended, nor should the composition be used for the treatment of acne and other severe skin conditions.

In conclusion, when applied after shaving, the composition as described is effective in reducing the inflammation and irritation commonly associated with pseudofolliculitis, and in initiating repair of skin damaged by any method of removing unwanted hair.

What is claimed is:

1. A post hair removal skin care lotion for use in reducing inflammation and irritation of skin following hair removal by shaving, waxing, tweezing, electrolysis, or use of depilatory products, comprising:

hydrocortisone acetate;

aloe vera gel;

tocopherol;

ascorbic acid; and soybean oil.

2. The post hair removal skin care lotion as recited in claim 1, further comprising alpha lipoic acid.

3. The post hair removal skin care lotion as recited in claim 2, wherein the composition further comprises a vehicle of deionized water, and an emulsifying agent, and wherein the hydrocortisone acetate is present at 0.180–0.500% of the total mixture.

4. The post hair removal skin care lotion as recited in claim 3, wherein the emulsifying agent includes stearic acid.

5. The post hair removal skin care lotion as recited in claim 4, wherein the emulsifying agent also includes glyceryl monostearate.

6. The post hair removal skin care lotion as recited in claim 5, wherein the soybean oil is present at substantially between 6.021–7.359% of the total mixture.

7. The post hair removal skin care lotion as recited in claim 6, further comprising a preservative.

8. The post hair removal skin care lotion as recited in claim 7, wherein the preservative includes methylparaben, propylparaben, and polyquaternium-15.

9. The post hair removal skin care lotion as recited in claim 8, further comprising a thickening agent.

10. The post hair removal skin care lotion as recited in claim 9, wherein the thickening agent includes carbomer and hydroxypropyl methylcellulose.

11. The post hair removal skin care lotion as recited in claim 10, further comprising propylene glycol.

12. The post hair removal skin care lotion as recited in claim 11, further comprising lauramide DEA.

13. The post hair removal skin care lotion as recited in claim 12, wherein the weight percentage composition of the components of the mixture are aloe vera gel at a weight percent of 6.021–7.359%, stearic acid at a weight percent of 3.51–4.29%, glyceryl monostearate at a weight percent of 3.006–3.674%, propylene glycol at a weight percent of 2.511–3.069%, lauramide DEA at a weight percent of 1.35–1.55%, tocopherol at a weight percent of 0.405–0.495%, hydrocortisone acetate at a weight percent of 0.180–0.500%, ascorbic acid at a weight percent of 0.198–0.242%, carbomer at a weight percent of 0.198–0.242%, hydroxypropyl methylcellulose at a weight percent of 0.198–0.242%, methylparaben at a weight percent of 0.198–0.242%, propylparaben at a weight percent of 0.099–0.121%, and polyquaternium-15 at a weight percent of 0.09–0.11%.

14. A post hair removal skin care method, for reducing inflammation and irritation associated with pseudofolliculitis, using a composition comprising hydrocortisone acetate, aloe vera gel, tocopherol, alpha lipoic acid, ascorbic acid, and soybean oil, comprising the steps of:

a) removing air from an anatomical area; and b) applying the mixture to the anatomical area immediately following step (a).

15. The post hair removal skin care method as recited in claim 14 wherein hydrocortisone acetate is present at 0.18–0.5%, aloe vera gel is present at 6.021–7.359%, tocopherol acetate is present at 0.405–0.495%, ascorbic acid is present at 0.198–0.242%, and soybean oil is present at 6.021–7.359%, and wherein these components are provided in a vehicle of deionized water.

16. The therapeutic after-shave care method as recited in claim 15 wherein the components further include an emulsifying agent, a thickening agent, and a preservative.

* * * * *